United States Patent [19]

Peterson

[11] Patent Number: 5,494,680
[45] Date of Patent: Feb. 27, 1996

[54] TRANSDERMAL DELIVERY DEVICE

[75] Inventor: Timothy A. Peterson, Lino Lakes, Minn.

[73] Assignee: Minnesota Mining and Manufacturing Company, St. Paul, Minn.

[21] Appl. No.: 164,054

[22] Filed: Dec. 8, 1993

[51] Int. Cl.⁶ .................................................. A61F 13/00
[52] U.S. Cl. .......................................... 424/448; 424/449
[58] Field of Search ...................... 424/448, 449

[56] References Cited

U.S. PATENT DOCUMENTS

| | | | |
|---|---|---|---|
| 4,060,084 | 11/1977 | Chandrasekaran et al. | 128/260 |
| 4,751,087 | 6/1988 | Wick | 424/449 |
| 4,801,458 | 1/1989 | Hidaka | 424/443 |
| 4,880,633 | 11/1989 | Loper et al. | 424/449 |
| 4,994,267 | 2/1991 | Sablotsky | 424/78 |
| 5,006,342 | 4/1991 | Cleary et al. | 424/445 |
| 5,176,917 | 1/1993 | Müller | 424/448 |
| 5,223,261 | 6/1993 | Nelson et al. | 424/443 |
| 5,409,946 | 4/1995 | Garvey et al. | 514/372 |

FOREIGN PATENT DOCUMENTS

92/05811  4/1992  WIPO.
92/21339  12/1992  WIPO.

OTHER PUBLICATIONS

*CRC Critical Reviews in Therapeutic Drug Carrier Systems*, 1987, vol. 4, Issue 1, 13–37 (Knepp et al.).

Primary Examiner—D. Gabrielle Phelan
Attorney, Agent, or Firm—Gary L. Griswold; Walter N. Kirn; Robert H. Brink

[57] ABSTRACT

A transdermal drug delivery device involving a backing bearing at least one adhesive layer of an acrylate copolymer and a therapeutically effective amount of (S)-3-methyl-5-(1-methyl-2-pyrrolidinyl)isoxazole. The device optionally further involves (i) a second adhesive layer of an acrylate copolymer and optionally a therapeutically effective amount of (S)-3-methyl-5-(1-methyl-2-pyrrolidinyl)isoxazole, and (ii) a membrane intermediate the first and second adhesive layers.

27 Claims, 1 Drawing Sheet

TRANSDERMAL DELIVERY DEVICE

BACKGROUND OF THE INVENTION

1. Field of the Invention

This invention relates to transdermal drug delivery devices. In another aspect this invention relates to pharmaceutical formulations containing (S)-3-methyl-5-(1-methyl-2-pyrrolidinyl)isoxazole.

2. Description of the Related Art

Transdermal drug delivery devices are designed to deliver a therapeutically effective amount of drug across the skin of a patient. Devices known to the art include reservoir type devices involving membranes that control the rate of drug release to the skin and devices involving a dispersion of the drug in a matrix such as a pressure sensitive adhesive. The skin however presents a substantial barrier to ingress of foreign substances into the body. It is therefore often desirable or necessary to incorporate certain materials that enhance the rate at which the drug passes through the skin. However the type of device, the transdermal flux rate that is suitable, and the suitable formulation components are dependent upon the particular drug to be delivered.

(S)-3-Methyl-5-(1-methyl-2-pyrrolidinyl)isoxazole is disclosed in International Publication Number WO 92/21339 and is described as a selective and potent agonist at neuronal nicotinic acetylcholine receptors. It is said to be potentially useful in the treatment of cognitive, neurological and mental disorders characterized by decreased cholinergic function, such as, for example dementias, attentional hyperactivity disorder and anxiety associated with cognitive impairment and substance abuse withdrawal.

SUMMARY OF THE INVENTION

The present invention provides a transdermal delivery device comprising:

(A) a backing;
(B) an adhesive layer adhered to one surface of the backing and comprising a homogeneous mixture of
  (1) a copolymer comprising
    (a) about 80 to 98 percent by weight of an alkyl acrylate or methacrylate containing 4 to 10 carbon atoms in the alkyl group, based on the weight of all monomers in the copolymer; and
    (b) about 2 to 20 percent by weight of a monomer selected from the group consisting of acrylic acid, methacrylic acid, an alkyl acrylate or methacrylate containing 1 to 3 carbon atoms in the alkyl group, acrylamide, methacrylamide, a lower alkyl substituted acrylamide, diacetone acrylamide and N-vinyl- 2-pyrrolidone, based on the weight of all monomers in the copolymer; and
  (2) a therapeutically effective amount of (S)-3-methyl-5-(1-methyl-2-pyrrolidinyl)isoxazole.

The present invention also provides a transdermal delivery device comprising:

(A) a backing;
(B) an adhesive layer adhered to one surface of the backing and comprising a homogeneous mixture of
  (1) a copolymer comprising
    (a) about 60 to 80 percent by weight of an alkyl acrylate or methacrylate containing 4 to 10 carbon atoms in the alkyl group, based on the weight of all monomers in the copolymer;
    (b) about 4 to 9 percent by weight of a monomer selected from the group consisting of acrylic acid, methacrylic acid, an alkyl acrylate or methacrylate containing 1 to 3 carbon atoms in the alkyl group, acrylamide, methacrylamide, a lower alkyl substituted acrylamide, diacetone acrylamide and N-vinyl-2-pyrrolidone, based on the weight of all monomers in the copolymer; and
    (c) about 15 to 35 percent by weight of vinyl acetate, based on the weight of all monomers in the copolymer; and
  (2) a therapeutically effective amount of (S)-3-methyl-5-(1-methyl-2-pyrrolidinyl)isoxazole.

The present invention also provides a transdermal delivery device comprising:

(A) a backing;
(B) a first adhesive layer adhered to one surface of the backing and comprising an adhesive selected from the group consisting of:
  (1) a copolymer comprising
    (a) about 80 to 98 percent by weight of an alkyl acrylate or methacrylate containing 4 to 10 carbon atoms in the alkyl group, based on the weight of all monomers in the copolymer; and
    (b) about 2 to 20 percent by weight of a monomer selected from the group consisting of acrylic acid, methacrylic acid, an alkyl acrylate or methacrylate containing 1 to 3 carbon atoms in the alkyl group, acrylamide, methacrylamide, a lower alkyl substituted acrylamide, diacetone acrylamide and N-vinyl-2-pyrrolidone, based on the weight of all monomers in the copolymer; and
  (2) a copolymer comprising
    (a) about 60 to 80 percent by weight of an alkyl acrylate or methacrylate containing 4 to 10 carbon atoms in the alkyl group, based on the weight of all monomers in the copolymer;
    (b) about 4 to 9 percent by weight of a monomer selected from the group consisting of acrylic acid, methacrylic acid, an alkyl acrylate or methacrylate containing 1 to 3 carbon atoms in the alkyl group, acrylamide, methacrylamide, a lower alkyl substituted acrylamide, diacetone acrylamide and N-vinyl-2-pyrrolidone, based on the weight of all monomers in the copolymer; and
    (c) about 15 to 35 percent by weight of vinyl acetate, based on the weight of all monomers in the copolymer;
(C) a second adhesive layer comprising an adhesive selected from the group consisting of:
  (1) a copolymer comprising
    (a) about 80 to 98 percent by weight of an alkyl acrylate or methacrylate containing 4 to 10 carbon atoms in the alkyl group, based on the weight of all monomers in the copolymer; and
    (b) about 2 to 20 percent by weight of a monomer selected from the group consisting of acrylic acid, methacrylic acid, an alkyl acrylate or methacrylate containing 1 to 3 carbon atoms in the alkyl group, acrylamide, methacrylamide, a lower alkyl substituted acrylamide, diacetone acrylamide and N-vinyl-2-pyrrolidone, based on the weight of all monomers in the copolymer; and
  (2) a copolymer comprising
    (a) about 60 to 80 percent by weight of an alkyl acrylate or methacrylate containing 4 to 10 carbon atoms in the alkyl group, based on the weight of all monomers in the copolymer;

(b) about 4 to 9 percent by weight of a monomer selected from the group consisting of acrylic acid, methacrylic acid, an alkyl acrylate or methacrylate containing 1 to 3 carbon atoms in the alkyl group, acrylamide, methacrylamide, a lower alkyl substituted acrylamide, diacetone acrylamide and N-vinyl-2-pyrrolidone, based on the weight of all monomers in the copolymer; and (c) about 15 to 35 percent by weight of vinyl acetate, based on the weight of all monomers in the copolymer; and (D) a membrane between the first and second adhesive layers, the membrane being permeable to (S)-3-methyl-5-(1-methyl-2-pyrrolidinyl)isoxazole, wherein at least one of said first and second adhesive layers further comprises a therapeutically effective amount of (S)-3-methyl-5-(1-methyl-2-pyrrolidinyl)isoxazole in admixture therewith.

DETAILED DESCRIPTION OF THE INVENTION

Figure 1:
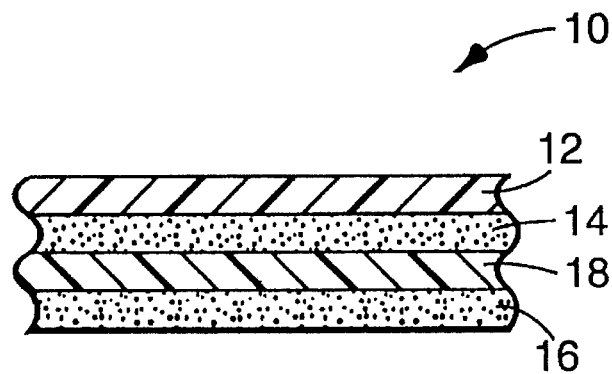
FIG. 1 shows a section through an embodiment of the present invention containing first and second adhesive layers with a membrane between the layers.

The present invention provides transdermal drug delivery devices containing (S)-3-methyl-5-(1-methyl-2-pyrrolidinyl)isoxazole (sometimes referred to herein as "the drug").

(S)-3-methyl-5-(1-methyl-2-pyrrolidinyl)isoxazole is known and disclosed in International Publication Number WO 92/21339 (Garvey et al.), Examples 1 and 2 thereof being incorporated herein by reference. The (S)-3-methyl-5-(1-methyl-2-pyrrolidinyl)isoxazole is present in a transdermal delivery device of the invention in a therapeutically effective amount. The amount that constitutes a therapeutically effective amount varies according to the condition being treated, the surface area of the skin over which the device is to be placed, and other components of the transdermal delivery device. Accordingly it is not practical to enumerate particular preferred amounts but such can be readily determined by those skilled in the art with due consideration of these factors. Generally, however, (S)-3-methyl-5-(1-methyl-2-pyrrolidinyl)isoxazole is present in at least one adhesive layer of a device of the invention in an amount of about 5 to 35 percent, preferably about 10 to 30 percent, by weight based on the total weight of the adhesive layer that contains the drug. In those embodiments of the invention involving both a first and a second adhesive layer either or both of such adhesive layers can contain the drug.

The drug exhibits substantial solubility in the copolymer component of the adhesive layer (described in detail below). Accordingly in a preferred embodiment of the invention the drug is substantially fully dissolved in the copolymer.

The adhesive layer or layers in a device of the invention are generally about 25–600 μm thick. The adhesives utilized in the practice of the invention should be substantially chemically inert to (S)-3-methyl- 5-(1-methyl-2-pyrrolidinyl)isoxazole. Suitable acrylic copolymer pressure sensitive adhesives for use in one embodiment of the invention comprise in an amount of about 80 to 98 percent by weight (based on the total weight of all the monomers in the copolymer), preferably 85 to 91 percent by weight of an alkyl acrylate or methacrylate containing in the alkyl group 4 to 10 carbon atoms, preferably 6 to 10 carbon atoms, more preferably about 6 to 8 carbon atoms, and most preferably 8 carbon atoms. Examples of suitable alkyl acrylates are n-butyl, n-pentyl, n-hexyl, isoheptyl, n-nonyl, n-decyl, isohexyl, 2-ethyloctyl, isooctyl and 2-ethylhexyl acrylates. The most preferred alkyl acrylate is isooctyl acrylate. These adhesives further comprise from about 2 to 20 percent by weight (based on the total weight of all the monomers in the copolymer) of a monomer selected from the group consisting of acrylic acid, methacrylic acid, an alkyl acrylate or methacrylate containing 1 to 3 carbon atoms in the alkyl group, acrylamide, methacrylamide, a lower alkyl substituted acrylamide, diacetone acrylamide and N-vinyl- 2-pyrrolidone. The preferred monomers are acrylic acid, acrylamide and N-vinyl-2-pyrrolidone.

In another embodiment of the invention, the acrylic copolymer pressure sensitive adhesive comprises in an amount of about 60 to 80 percent by weight (based on the total weight of all the monomers in the copolymer), preferably 70 to 80 percent by weight of an alkyl acrylate or methacrylate containing in the alkyl group 4 to 10 carbon atoms, preferably 6 to 10 carbon atoms, more preferably about 6 to 8 carbon atoms, and most preferably 8 carbon atoms. Examples of suitable alkyl acrylates are n-butyl, n-pentyl, n-hexyl, isoheptyl, n-nonyl, n-decyl, isohexyl, 2-ethyloctyl, isooctyl and 2-ethylhexyl acrylates. The most preferred alkyl acrylate is isooctyl acrylate. These adhesives further comprise from about 4 to 9 percent by weight (based on the total weight of all the monomers in the copolymer) of a monomer selected from the group consisting of acrylic acid, methacrylic acid, an alkyl acrylate or methacrylate containing 1 to 3 carbon atoms in the alkyl group, acrylamide, methacrylamide, a lower alkyl substituted acrylamide, diacetone acrylamide and N-vinyl-2-pyrrolidone. The preferred monomer is acrylamide. These adhesives further comprise from about 15 to 35 percent by weight (based on the total weight of all the monomers in the copolymer), and preferably 15 to 25 percent by weight of vinyl acetate.

Since pressure sensitive adhesives such as those described above are inherently tacky and are suitably heat and light stable, there is no need to add tackifiers or stabilizers. However, such can be added if desired. The pressure sensitive adhesives can further comprise a reinforcer (e.g., colloidal silicon dioxide) if desired.

It has been found that the addition of certain skin penetration enhancers increases the penetration of (S)-3-methyl-5-(1-methyl-2-pyrrolidinyl)isoxazole in vitro compared to a like device not containing the skin penetration enhancer when this phenomena is measured using the skin penetration model described below. Hence, the transdermal delivery devices of the invention can optionally further comprise a skin penetration enhancer. Exemplary skin penetration enhancers are disclosed, e.g., in *J. Controlled Release*, 1993, 25, 1 (Santus et al.), and include fatty acids, fatty acid esters of lower (i.e., $C_1$-$C_4$) alcohols, fatty acid monoglycerides, and fatty alcohols. Skin penetration enhancers that have been found to be suitable include lauryl alcohol, oleyl alcohol, and ethyl oleate.

A transdermal delivery device of the invention also comprises a backing. The backing is flexible such that the device conforms to the skin. Suitable backing materials include conventional flexible backing materials used for pressure sensitive tapes, such as polyethylene, particularly low density polyethylene, linear low density polyethylene, high density polyethylene, polyester polyethylene terephthalate, randomly oriented nylon fibers, polypropylene, ethylene-vinyl acetate copolymer, polyurethane, rayon and the like. Backings that are layered, such as polyethylene-aluminum-polyethylene composites, are also suitable. The backing should be substantially inert to the ingredients of the adhesive layer.

Some embodiments of the invention also comprise a membrane. Physiologically acceptable membranes that have adequate permeability to (S)-3-methyl-5-(1-methyl- 2-pyrrolidinyl)isoxazole are suitable for use in the devices of the invention. Examples of suitable materials for the manufacture of these membranes include polyethylene, low density polyethylene, linear low density polyethylene, high density polyethylene, polyurethane, nylon, and ethylene:vinyl acetate copolymers. Membranes prepared from linear low density polyethylene and ethylene:vinyl acetate copolymers are preferred. Examples of suitable physical forms for the membrane include a continuous film (e.g., polyethylene films), a macroporous membrane (e.g., polyethylene thermal formed netting), or a microporous membrane (e.g., a polyethylene membrane such as COTRAN™ 9710 membrane, 3M). The membrane serves to improve the structural integrity of a device of the invention. Further the membrane can be rate controlling, i.e., the presence of the membrane in the transdermal device changes the skin penetration profile of the device compared to a like device not having the membrane, as such profile is determined using the test method described below. The membrane thickness will generally be from about 1 to 4 mil (25 to 100 μm).

It is desirable for a transdermal device to have sufficiently little cold flow such that it is stable upon storage. It is also required that it adhere well to the skin. In order to achieve optimal adhesion and resistance to cold flow, at least the skin contacting adhesive layer (and preferably both adhesive layers if the device contains two adhesive layers) preferably has a compliance value (measured according to the test method set forth in detail below) of $2 \times 10^{-5}$ to $4 \times 10^{-5}$ cm$^2$/dyne. Compliance values outside this range are also suitable, but those adhesive layers having substantially lower compliance values will generally have less than optimal adhesion to skin. Those having substantially higher compliance values will generally have less than optimal cold flow and might leave residual adhesive when removed from the skin. Compliance is influenced by the chain length, degree of crosslinking (if any), and the constituent monomers in the adhesive copolymers. Furthermore the drug and other excipients (e.g., skin penetration enhancers) function to soften the adhesive copolymers and therefore the amount of such components present in the adhesive layers also affects compliance. Adhesive layers having optimal compliance can be readily selected and prepared by those skilled in the art with due consideration of the factors affecting compliance.

The adhesive copolymers described above for use in a device of the invention can be prepared by methods well known to those skilled in the art and described, for example, in U.S. Pat. No. RE 24,906 (Ulrich), the disclosure of which is incorporated herein by reference. The polymerization reaction can be carried out using a free radical initiator such as an organic peroxide (e.g., benzoylperoxide) or an organic azo compound (e.g., 2,2'-azobis(2,4-dimethylpentanenitrile)).

Transdermal delivery devices of the invention which comprise a backing and a single layer of adhesive are preferably prepared by combining adhesive and (S)- 3-methyl-5-(1-methyl-2-pyrrolidinyl)isoxazole with an organic solvent (e.g., ethyl acetate and methanol) to afford a coating formulation. The total solids content of the coating formulation is preferably in a range of about 15 to 40 percent by weight, and more preferably in the range of about 20 to 35 percent by weight, based on the total weight of the coating formulation. The mixture of adhesive, (S)-3-methyl-5-(1-methyl-2-pyrrolidinyl)isoxazole and solvent is shaken at high speed until a homogeneous formulation is obtained, then allowed to stand to dissipate air bubbles. The resulting coating formulation is knife coated onto a suitable release liner to provide a predetermined uniform thickness of the coating formulation. Suitable release liners include conventional release liners comprising a known sheet material such as a polyester web, a polyethylene web, or a polystyrene web, or a polyethylene-coated paper, coated with a suitable fluoropolymer or silicone based coating. The coated release liner is then dried and then laminated onto a backing material using conventional methods.

An exemplary transdermal delivery device of the invention involving two adhesive layers and an intermediate membrane is shown in FIG. 1. Device 10 comprises a backing 12, first adhesive layer 14, second adhesive layer 16 and membrane 18. Device 10 is prepared in two portions which are then laminated together to form the final device. The upper (skin distal) portion of the device is prepared as described above for a device comprising a single layer of adhesive by coating a formulation containing adhesive, (S)-3-methyl-5-(1-methyl-2-pyrrolidinyl)isoxazole and solvent onto a release liner, drying the coated release liner then laminating to backing 12. The lower portion is prepared by coating a formulation containing adhesive, optionally (S)-3-methyl-5-(1-methyl-2-pyrrolidinyl)isoxazole and solvent onto a release liner, drying the coated release liner and then laminating to membrane 16. The release liner is removed from the upper portion and it is laminated to the membrane surface of the lower portion to afford the final device. The coating formulation used to prepare the upper portion can differ (e.g., it can contain a different adhesive or a different concentration of (S)- 3-methyl-5-(1-methyl-2-pyrrolidinyl)isoxazole) from that used to prepare the lower portion. The thickness of the first adhesive layer can differ from that of the second adhesive layer.

The transdermal delivery devices of the invention can be made in the form of an article such as a tape, a patch a sheet, a dressing or any other form known to those skilled in the art. Generally the device will be in the form of a patch of a size suitable to deliver a preselected amount of (S)-3-methyl-5-(1-methyl-2-pyrrolidinyl)isoxazole through the skin. Generally the device will have a surface area of about 1 cm$^2$ to about 40 cm$^2$.

The examples set forth below are intended to illustrate the invention.

Preparation of Adhesive Copolymers

The adhesive copolymers used in the examples that follow were prepared generally according to the methods described below. The inherent viscosity values which are reported were measured by conventional means using a Cannon-Fenske #50 viscometer in a water bath controlled at 25° C. to measure the flow time of 10 milliliters of a polymer solution (0.15 g per deciliter of polymer in ethyl acetate).

Preparation of Isooctyl Acrylate: Acrylic Acid (94:6) Copolymer

Isooctyl acrylate (173.9 g), acrylic acid (11.1 g) azobisisobutyronitrile (0.37 g), ethyl acetate (313.425 g) and isopropanol (1.575 g) were placed in a 1 quart (946 mL) bottle. The mixture was deoxygenated by purging with nitrogen (1 L/min) for 2 minutes. The bottle was sealed and placed in a 55° C. rotating water bath for 24 hours to effect essentially complete polymerization. The inherent viscosity in ethyl acetate was 0.97 deciliter/gram.

Preparation of Isooctyl Acrylate: Acrylic Acid (90: 10) Copolymer

Isooctyl acrylate (21.6 g), acrylic acid (2.4 g), 2,2'-azobis (2,4-dimethylpentanenitrile) (0.05 g, VAZO™ 52, DuPont), ethyl acetate (34.2 g) and isopropanol (1.8 g) were placed in a 4 ounce (120 mL) bottle. The mixture was deoxygenated by purging with nitrogen (1 L/min) for 2 minutes. The bottle was sealed and placed in a 45° C. rotating water bath for 24 hours. The bottle was opened and 0.05 g of 2,2'-azobis(2, 4-dimethylpentanenitrile) was added. The solution was deoxygenated as above, sealed and placed into the water bath for another 24 hours at 45° C. The inherent viscosity in ethyl acetate was 0.651 deciliter/gram.

Preparation of Isooctyl Acrylate: Acrylic Acid (85:15) Copolymer

This copolymer was prepared according to the method used to prepare the 90:10 copolymer except that the initial charge contained 20.4 g of isooctyl acrylate and 3.6 g of acrylic acid. The inherent viscosity in ethyl acetate was 0.606 deciliter/gram.

Preparation of Isooctyl Acrylate: Acrylic Acid (80:20) Copolymer

This copolymer was prepared according to the method used to prepare the 90:10 copolymer except that the initial charge contained 19.2 g of isooctyl acrylate and 4.8 g of acrylic acid. The inherent viscosity in ethyl acetate was 0.603 deciliter/gram.

Preparation of Isooctyl Acrylate: N-vinyl-2-pyrrolidone (91:9) Copolymer

Isooctyl acrylate (54.9 Kg), N-vinyl-2-pyrrolidone (5.4 Kg), and ethyl acetate (93.6 Kg) were charged into a 75 gallon (285 liter) stainless steel reactor. The mixture was deoxygenated and heated to 55° C. After 5 minutes at 55° C., azobisisobutyronitrile (30 g) premixed in ethyl acetate (1 Kg) was charged to the reactor. Additional portions of azobisisobutyronitrile (30 g) premixed with ethyl acetate (1 Kg) were added 4 hours after the start of the reaction and again at 8 hours. The temperature was maintained at 55° C. throughout the reaction. The reaction was continued until complete. An antioxidant (61 g, IRGANOX™ 1010, Ciba-Geigy Corp.) and heptane (66.3 Kg) were added to the reactor and the contents mixed until homogeneous. The final copolymer had a measured inherent viscosity of 1.67 deciliter/g in ethyl acetate.

Preparation of Isooctyl Acrylate: Acrylamide: Vinyl Acetate (75:5:20) Copolymer

A master batch was prepared by combining isooctyl acrylate (621.0 g), acrylamide (41.4 g), vinyl acetate (165.6 g), 2,2'azobis(2,4-dimethylpentanenitrile) (1.656 g, VAZO™ 52, DuPont), ethyl acetate (884.5 g) and methanol (87.48 g). A portion (400 g) of the resulting solution was placed in a one quart (0.95 liter) amber glass bottle. The bottle was purged for 2 minutes with nitrogen at a flow rate of 1 liter per minute. The bottle was sealed and placed in a rotating water bath at 45° C. for 24 hours to effect essentially complete polymerization. The copolymer was diluted with ethyl acetate: methanol (250 g, 90:10 volume-to-volume) to 26.05% solids and had a measured inherent viscosity of 1.27 deciliter/g in ethyl acetate at a concentration of 0.15 g/deciliter.

Preparation of Isooctyl Acrylate: Acrylamide: Vinyl Acetate (74:6:20) Copolymer

Isooctyl acrylate (148 g), acrylamide (12 g), vinyl acetate (40 g), 2,2'azobis(2,4-dimethylpentanenitrile) (0.30 g), ethyl acetate (310 g) and methanol (30.7 g) were added to a glass bottle. The bottle was purged with nitrogen for 3 minutes at a flow rate of 1 liter per minute. The bottle was sealed and placed in a rotating water bath at 45° C. for 29.5 hours to effect essentially complete polymerization. The inherent viscosity in ethyl acetate was 1.20 deciliter/g.

Preparation of "Dry Adhesive"

Dry adhesive was prepared by knife coating a 25 to 30 percent solids solution of the adhesive copolymer at a thickness of 20–25 mil (500–635 μm) onto a release liner. The adhesive coated release liner was oven dried (3 minutes at 65° C., 3 minutes at 135° C., then 3 minutes at 177° C.) to remove solvent. The dried adhesive copolymer was then stripped off the release liner and stored in a glass container.

Membranes

Some of the membranes used in the examples below are commercially available (e.g., COTRAN™ 9720 polyethylene film and COTRAN™ 9702 controlled caliper membrane, both from 3M Company). Others were prepared from commercially available resins using conventional extrusion methods (e.g., thermal extrusion onto a quenching roll). Examples of suitable resins include ULTRATHENE™ ethylene-vinyl acetate (EVA) copolymers from Quantum Chemical, ELVAX™ EVA copolymers from DuPont and DOWLEX linear low density polyethylene resins from Dow Chemical Company. In the examples that follow, the designation "X% EVA" means a membrane prepared from an ethylene-vinyl acetate copolymer which contains X% vinyl acetate incorporated.

Compliance Test Method

The compliance values given in the examples below were obtained using a modified version of the Creep Compliance Procedure described in U.S. Pat. No. 4,737,559 (Kellen), the disclosure of which is incorporated herein by reference. The release liner is removed from a sample of the material to be tested. The exposed adhesive surface is folded back on itself in the lengthwise direction to produce a "sandwich" configuration, i.e., backing/adhesive/backing. The "sandwiched" sample is passed through a laminator then two test samples of equal area are cut using a rectangular die. One test sample is centered on the stationary plate of a shear-creep rheometer with the long axis of the test sample centered on the short axis of the plate. The small, non-stationary plate of the shear creep rheometer is centered over the first sample on the stationary plate such that the hook is facing up and toward the front of the rheometer. The second test sample is centered on the upper surface of the small, non-stationary plate matching the axial orientation of the first test sample. The large, non-stationary plate is placed over the second test sample and the entire assembly is clamped into place. The end of the small, non-stationary plate that is opposite the end with the hook is connected to a chart recorder. A string is connected to the hook of the small, non-stationary plate and extended over the front pulley of the rheometer. A weight (500 g) is attached to the free end of the string. The chart recorder is started and at the same time the weight is quickly released so that it hangs free. The weight is removed after exactly 3 minutes has elapsed. The displacement is read from the chart recorder. The compliance is then calculated using the equation:

$$J = 2 \frac{AX}{hf}$$

where A is the area of one face of the test sample, h is the thickness of the adhesive mass, X is the displacement and f is the force due to the weight attached to the string. Where A is expressed in cm², h in cm, X in cm and f in dynes, the compliance value J is given in cm²/dyne.

In Vitro Skin Penetration Test Method

Figure 2:
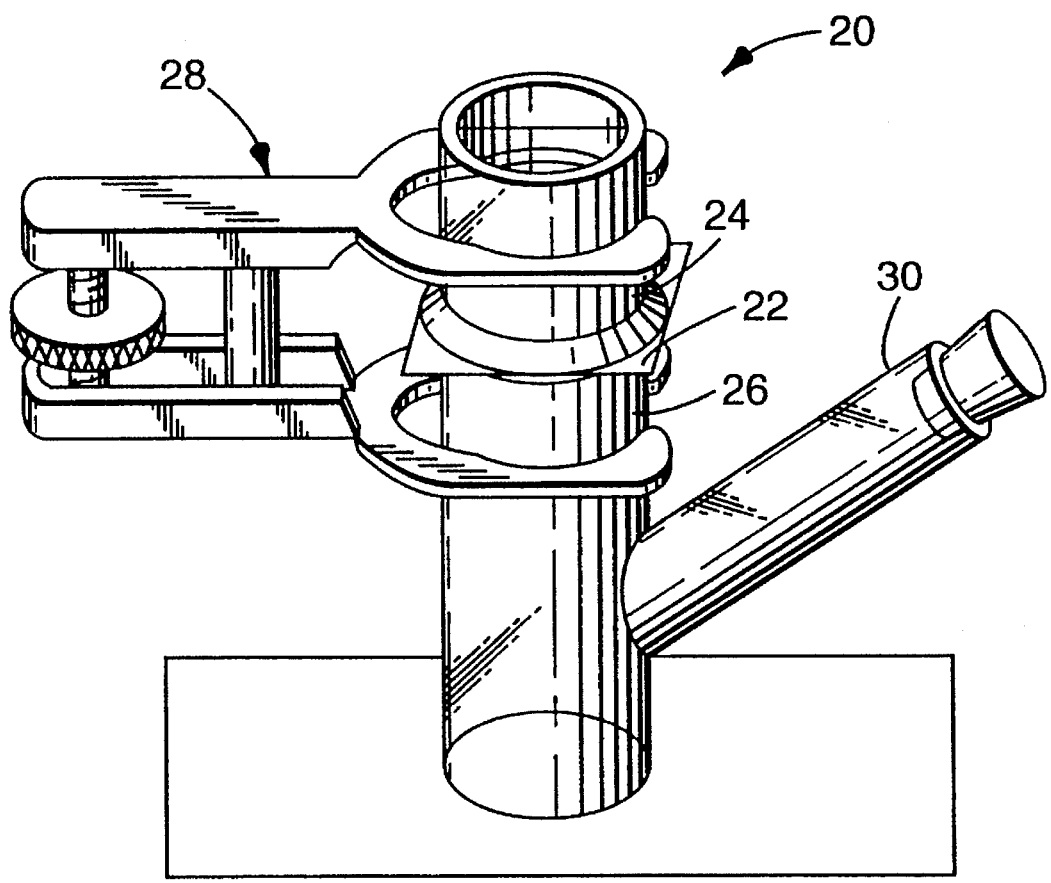
FIG. 2 shows a perspective view of a diffusion cell used to determine skin penetration rates.

The skin penetration data given in the examples below was obtained using the following test method. A Diffusion cell 20 of the type shown in FIG. 2 is used. Two types of skin are used, hairless mouse skin or human cadaver skin (Dermatomed skin about 500 μm thick obtained from a skin bank). As shown in FIG. 2, the skin 22 is mounted epidermal side up between upper portion 24 and lower portion 26 of the cell, which are held together by means of ball joint clamp 28.

The portion of the cell below the mounted skin is completely filled with receptor fluid (0.1M phosphate buffer, pH 6) such that the receptor fluid is in contact with the skin. The receptor fluid is stirred using a magnetic stir bar and a magnetic stirrer (not illustrated). The sampling port 30 is covered except when in use.

When a transdermal delivery device is evaluated, the skin is placed across the orifice of the lower portion of the diffusion cell, the release liner is removed from a 2.0 cm² patch and the patch is applied to the skin and pressed to cause uniform contact with the skin. The diffusion cell is assembled and the lower portion is filled with 10 mL of warm (32° C.) receptor fluid.

The cell is then placed in a constant temperature (32°±2° C.) and humidity (50±10% relative humidity) chamber. The receptor fluid is stirred by means of a magnetic stirrer throughout the experiment to assure a uniform sample and a reduced diffusion barrier on the dermal side of the skin. The entire volume of receptor fluid is withdrawn at specified time intervals and immediately replaced with fresh fluid. The withdrawn fluid is filtered through a 0.45 μm filter. A 1 mL portion of filtrate is then analyzed for (S)-3-methyl-5-(1-methyl-2-pyrrolidinyl)isoxazole using high performance liquid chromatography (Column: 15 cm×4.6 mm ZORBAX™ RX-C18 (DuPont), 5 μm particle size; Mobile Phase: acetonitrile/5 mM tetramethylammonium hydroxide aqueous solution/triethylamine, 50%/50%/0.1% v/v/v; Flow Rate: 1.5 mL/min; Detection: uv at 215 nm). The cumulative amount of (S)-3-methyl-5-(1-methyl-2-pyrrolidinyl)isoxazole penetrating the skin is calculated.

EXAMPLE 1

Dry adhesive (1.716 g of isooctyl acrylate:acrylic acid 94:6),(S)-3-methyl-5-(1-methyl-2-pyrrolidinyl)isoxazole (0.3005 g) and solvent (4.666 g of ethyl acetate:methanol 90:10 volume-to-volume) were placed in order in a glass vial. The vial was capped then agitated on a platform shaker until a uniform formulation was obtained. The formulation was knife coated at a thickness of 15 mil (381 μm) onto a silicone release liner. The resulting coated release liner was oven dried at 110° F. (43° C.) for 10 minutes. The resulting adhesive layer contained 85 percent by weight of the 94:6 isooctyl acrylate:acrylic acid copolymer and 15 percent by weight of (S)-3-methyl-5-( 1-methyl-2-pyrrolidinyl)isoxazole. The dried adhesive coated liner was laminated onto a polyethylene backing. The compliance was measured according to the test method described above. A J-value of $6.87 \times 10^{-5}$ cm²/dynes was obtained. Patches (2.0 cm²) were die cut from the laminate and the skin penetration through hairless mouse skin was determined using the test method described above. The skin penetration data is shown in Table 1 below. Each value is the average of two independent determinations.

EXAMPLE 2

Transdermal delivery devices were prepared according to the method of Example 1 except that the adhesive used was an isooctyl acrylate:N-vinylpyrrolidone 91:9 copolymer. The compliance was measured and a J-value of $6.47 \times 10^{-5}$ cm²/dynes was obtained. Skin penetration (hairless mouse skin) data is shown in Table 1 below. Each value is the average of two independent determinations.

EXAMPLE 3

Transdermal delivery devices were prepared according to the method of Example 1 except that the adhesive used was an isooctyl acrylate:acrylamide:vinyl acetate 75:5:20 copolymer. The compliance was measured and a J-value of $1.084 \times 10^{-5}$ cm²/dynes was obtained. The skin penetration (hairless mouse skin) data is shown in Table 1 below.

TABLE 1

| Example | Cumulative Amount Penetrating (μm/cm²) | | | | |
|---|---|---|---|---|---|
| Number | 4 hr | 8 hr | 12 hr | 24 hr | 48 hr |
| 1 | 193 | 348 | 464 | 628 | 754 |
| 2 | 446 | 657 | 739 | 775 | 779 |
| 3 | 269 | 452 | 566 | 655 | 673 |

EXAMPLES 4–9

Using the general method of Example 1 a set of transdermal delivery devices in which the weight percent of drug ((S)-3-methyl-5-(1-methyl-2-pyrrolidinyl)isoxazole) was varied was prepared. In each case the adhesive was an isooctyl acrylate:acrylamide:vinyl acetate 75:5:20 copolymer. The weight percent of drug and J-values are shown in Table 2 below. The skin penetration (human cadaver skin) data is shown in Table 3 below. Each value is the average of three independent determinations.

TABLE 2

| Example Number | Weight Percent Drug | J-value (cm²/dynes) |
|---|---|---|
| 4 | 5 | $0.362 \times 10^{-5}$ |
| 5 | 10 | $0.637 \times 10^{-5}$ |
| 6 | 5 | $0.770 \times 10^{-5}$ |
| 7 | 20 | $1.174 \times 10^{-5}$ |
| 8 | 25 | $1.462 \times 10^{-5}$ |
| 9 | 30 | $2.992 \times 10^{-5}$ |

TABLE 3

| Example | Cumulative Amount Penetrating (μm/cm²) | | | | | |
|---|---|---|---|---|---|---|
| Number | 2 hr | 4 hr | 8 hr | 12 hr | 24 hr | 48 hr |
| 4 | 33 | 51 | 65 | 71 | 75 | 75 |
| 5 | 125 | 195 | 246 | 263 | 273 | 274 |
| 6 | 198 | 317 | 411 | 446 | 471 | 475 |
| 7 | 249 | 400 | 521 | 565 | 596 | 601 |
| 8 | 364 | 592 | 753 | 800 | 825 | 828 |
| 9 | 503 | 921 | 1220 | 1327 | 1393 | 1401 |

EXAMPLES 10–13

Using the general method of Example 1, a set of transdermal delivery devices in which the weight percent of acrylic acid in the adhesive copolymer was varied was prepared. In each case the adhesive coating was prepared using ethyl acetate as the solvent and the resulting adhesive layer contained 15 percent by weight of (S)-3-methyl-5-(1-methyl-2-pyrrolidinyl)isoxazole. The adhesive copolymer used and J-values are shown in Table 4 below. The skin penetration (human cadaver skin) data is shown in Table 5 below. Each value is the average of three independent determinations.

TABLE 4

| Example Number | isooctyl acrylate: acrylic acid | J-value ($cm^2$/dynes) |
| --- | --- | --- |
| 10 | 94:6 | $6.369 \times 10^{-5}$ |
| 11 | 90:10 | $4.115 \times 10^{-5}$ |
| 12 | 85:15 | $0.7892 \times 10^{-5}$ |
| 13 | 80:20 | $0.2152 \times 10^{-5}$ |

TABLE 5

| Example Number | Cumulative Amount Penetrating ($\mu m/cm^2$) | | | | | |
| --- | --- | --- | --- | --- | --- | --- |
| | 2 hr | 4 hr | 8 hr | 12 hr | 24 hr | 48 hr |
| 10 | 139 | 269 | 427 | 520 | 646 | 730 |
| 11 | 115 | 230 | 381 | 475 | 613 | 722 |
| 12 | 34 | 71 | 132 | 181 | 277 | 378 |
| 13 | 18 | 38 | 72 | 103 | 170 | 254 |

EXAMPLES 14–16

Using the general method of Example 1 a set of transdermal delivery devices in which the weight percent of drug ((S)-3-methyl-5-(1-methyl-2-pyrrolidinyl)isoxazole) was varied was prepared. In each case the adhesive was an isooctyl acrylate:acrylic acid 85:15 copolymer. The weight percent of drug and J-values are shown in Table 6 below. The skin penetration (human cadaver skin) data is shown in Table 7 below. Each value is the average of three independent determinations.

TABLE 6

| Example Number | Weight Percent Drug | J-value ($cm^2$/dynes) |
| --- | --- | --- |
| 14 | 15 | $0.80 \times 10^{-5}$ |
| 15 | 25 | $4.37 \times 10^{-5}$ |
| 16 | 35 | $37.4 \times 10^{-5}$ |

TABLE 7

| Example Number | Cumulative Amount Penetrating ($\mu m/cm^2$) | | | | | |
| --- | --- | --- | --- | --- | --- | --- |
| | 2 hr | 4 hr | 8 hr | 12 hr | 24 hr | 48 hr |
| 14 | 20 | 48 | 89 | 121 | 192 | 298 |
| 15 | 46 | 110 | 197 | 260 | 389 | 523 |
| 16 | 346 | 677 | 1016 | 1207 | 1474 | 1666 |

EXAMPLES 17–19

Using the general method of Example 1 a set of transdermal delivery devices in which the weight percent of drug ((S)-3-methyl-5-(1-methyl-2-pyrrolidinyl)isoxazole) was varied was prepared. In each case the adhesive was an isooctyl acrylate:acrylic acid 80:20 copolymer. The weight percent of drug and J-values are shown in Table 8 below. The skin penetration (human cadaver skin) data is shown in Table 9 below. Each value is the average of three independent determinations.

TABLE 8

| Example Number | Weight Percent Drug | J-Value ($cm^2$/dynes) |
| --- | --- | --- |
| 17 | 25 | $0.406 \times 10^{-5}$ |
| 18 | 35 | $1.136 \times 10^{-5}$ |
| 19 | 45 | $21.73 \times 10^{-5}$ |

TABLE 9

| Example Number | Cumulative Amount Penetrating ($\mu m/cm^2$) | | | | | |
| --- | --- | --- | --- | --- | --- | --- |
| | 2 hr | 4 hr | 8 hr | 12 hr | 24 hr | 48 hr |
| 17 | 42 | 86 | 143 | 188 | 304 | 470 |
| 18 | 109 | 201 | 310 | 381 | 524 | 694 |
| 19 | 449 | 756 | 1063 | 1230 | 1472 | 1664 |

EXAMPLES 20–22

Using the general method of Example 1 a set of transdermal delivery devices in which the adhesive layer incorporated an adhesive reinforcer was prepared. In each example the adhesive used was an isooctyl acrylate:acrylamide:vinyl acetate 75:5:20 copolymer and 30 weight percent of (S)-3-methyl-5-(1-methyl-2-pyrrolidinyl)isoxazole was present. Colloidal silicon dioxide (AEROSIL™ 200 available from Degussa Corp, Teeterboro, N.J.) was used as the reinforcer and was added to the glass vial prior to shaking. The weight percent of silica used and the J-values are shown in Table 10 below. The skin penetration (human cadaver skin) data is shown in Table 11 below. Each value is the average of three independent determinations.

TABLE 10

| Example Number | Weight Percent Silica | J-Value ($cm^2$/dynes) |
| --- | --- | --- |
| 20 | 1 | $2.025 \times 10^{-5}$ |
| 21 | 2 | $1.584 \times 10^{-5}$ |
| 22 | 3 | $1.110 \times 10^{-5}$ |

TABLE 11

| Example Number | Cumulative Amount Penetrating ($\mu m/cm^2$) | | | | | |
| --- | --- | --- | --- | --- | --- | --- |
| | 2 hr | 4 hr | 8 hr | 12 hr | 24 hr | 48 hr |
| 20 | 591 | 921 | 1157 | 1243 | 1307 | 1319 |
| 21 | 560 | 926 | 1191 | 1281 | 1351 | 1370 |
| 22 | 506 | 820 | 1044 | 1124 | 1194 | 1216 |

EXAMPLES 23–28

Transdermal delivery devices having two distinct adhesive layers separated by a membrane were prepared as follows.

The first adhesive layer was prepared as follows. Dry adhesive (7.0034 g of isooctyl acrylate:acrylamide:vinyl acetate 75:5:20), (S)-3-methyl- 5-(1-methyl-2-pyrrolidinyl)isoxazole (3.0147 g) and solvent (32.045 g of ethyl acetate:methanol 90:10) were placed in order in a glass vial. The vial was capped then agitated on a platform shaker until a uniform formulation was obtained. The formulation was knife coated at a thickness of 18 mil (457 µm) onto a release liner (SCOTCHPAK™ 1022 fluoropolymer coated release liner from 3M Company). The resulting coated release liner was oven dried at 110° F. (43° C.) for 10 minutes. The resulting adhesive layer contained 70 percent by weight of the 75:5:20 isooctyl acrylate:acrylamide:vinyl acetate copolymer and 30 percent by weight of (S)-3-methyl-5-(1-methyl-2-pyrrolidinyl)isoxazole. The dried adhesive coated liner was allowed to cool for about 5 minutes then it was laminated onto a low density polyethylene backing (COTRAN™ 9720 polyethylene film available from 3M).

The second adhesive layer was prepared as follows. Dry adhesive (4.8051 g of isooctyl acrylate:acrylamide:vinyl acetate 75:5:20), (S)-3-methyl- 5-(1-methyl-2-pyrrolidinyl)isoxazole (1.1983 g) and solvent (18.013 g of ethyl acetate:methanol 90:10) were placed in order in a glass vial. The vial was agitated on a platform shaker until a uniform formulation was obtained. The formulation was knife coated at a thickness of 16 mil (406 μm) onto SCOTCHPAK™ 1022 fluoropolymer coated release liner. The resulting coated release liner was oven dried at 110° F. (43° C.) for 10 minutes. The resulting adhesive layer contained 80 percent by weight of the 75:5:20 isooctyl acrylate:acrylamide:vinylacetate copolymer and 20 percent by weight of (S)-3-methyl-5-(1-methyl-2-pyrrolidinyl)isoxazole. The dried adhesive coated liner was laminated onto one of the membranes shown in Table 12 below.

The release liner was removed from the first adhesive layer then the layer was laminated to the membrane on the second adhesive layer. Patches (2.0 cm$^2$) were die cut from the resulting laminate. Each patch consisted of five layers: a backing, a first adhesive layer containing 30 percent by weight of (S)-3-methyl- 5-(1-methyl-2-pyrrolidinyl)isoxazole, a membrane, a second adhesive layer containing 20 percent of (S)-3-methyl-5-(1-methyl-2-pyrrolidinyl)isoxazole, and a release liner. The skin penetration (human cadaver skin) data is shown in Table 13 below. Except as noted, each value is the average of three independent determinations.

TABLE 12

| Example Number | Membrane |
|---|---|
| 23 | 2% EVA film$^1$ (3 mil/76 μm) |
| 24 | 4.5% EVA film$^2$ (2 mil/51 μm) |
| 25 | 9% EVA films$^3$ (2 mil/51 μm) |
| 26 | 19% EVA film$^4$ (2 mil/51 μm) |
| 27 | polyurethane$^5$ (2 mil/51 μm) |
| 28 | microporous polyethylene$^6$ |

$^1$Prepared from NATR 187 Resin, Quantum Chemical
$^2$Prepared from NATR 198 Resin, Quantum Chemical
$^3$COTRAN ™ 9703, 3M
$^4$Prepared from ULTRATHENE ™ UE631-000, Quantum Chemical
$^5$Prepared from Dow Medical Grade 2363-80AE Resin
$^6$COTRAN ™ 9710, 3M

TABLE 13

| Example Number | Cumulative Amount Penetrating (μm/cm$^2$) | | | | | |
|---|---|---|---|---|---|---|
| | 2 hr | 4 hr | 8 hr | 12 hr | 24 hr | 48 hr |
| 23 | 352$^1$ | 604$^1$ | 840$^1$ | 974$^1$ | 1177$^1$ | 1289$^1$ |
| 24 | 119 | 244 | 416 | 544 | 805 | 987 |
| 25 | 318$^1$ | 607$^1$ | 913$^1$ | 1092$^1$ | 1316$^1$ | 1428$^1$ |
| 26 | 86$^1$ | 240$^1$ | 474$^1$ | 639$^1$ | 953$^1$ | 1229$^1$ |
| 27 | 258$^1$ | 481$^1$ | 750$^1$ | 921$^1$ | 1166$^1$ | 1318$^1$ |
| 28 | 307 | 576 | 869 | 1038 | 1262 | 1394 |

$^1$Average of 2 independent determinations

EXAMPLES 29–37

Using the general method of Example 23, a set of multilayer transdermal delivery devices was prepared. The compositions are shown in Table 14 below. In each example the drug is (S)-3-methyl-5-(1-methyl-2-pyrrolidinyl)isoxazole and the percent is by weight based on the total weight of the adhesive layer. All of the membranes used were 3 mil (76 μm) thick. The skin penetration (human cadaver skin) data is shown in Table 15 below. Each value is the average of three independent determinations.

TABLE 14

| Example Number | First Adhesive Layer | Membrane | Second Adhesive Layer |
|---|---|---|---|
| 29 | 30% drug 70% IOA:AA$^1$ | 9% EVA$^3$ | No drug IOA:ACM:VA$^2$ |
| 30 | 30% drug 70% IOA:AA | 9% EVA$^3$ | No drug IOA:ACM:VA |
| 31 | 30% drug 70% IOA:AA | 9% EVA$^3$ | 20% drug 80% IOA:ACM:VA |
| 32 | 30% drug 70% IOA:AA | None | No drug IOA:ACM:VA |
| 33 | 30% drug 70% IOA:AA | None | 20% drug 80% IOA:ACM:VA |
| 34 | 30% drug 70% IOA:ACM:VA | low density polyethylene$^4$ | 20% drug 80% IOA:ACM:VA |
| 35 | 30% drug 70% IOA:ACM:VA | 9% EVA$^3$ | 20% drug 80% IOA:ACM:VA |
| 36 | 30% drug 70% IOA:ACM:VA | low density polyethylene$^4$ | No drug IOA:ACM:VA |
| 37 | 30% drug 70% IOA:ACM:VA | 9% EVA$^3$ | No drug IOA:ACM:VA |

$^1$IOA:AA is isooctyl acrylate:acrylic acid 80:20 copolymer
$^2$IOA:ACM:VA is isooctyl acrylate:acrylamide:vinyl acetate 75:5:20 copolymer
$^3$COTRAN ™ 9703, 3M
$^4$COTRAN ™ 9720, 3M

TABLE 15

| Example Number | Cumulative Amount Penetrating (μm/cm$^2$) | | | | |
|---|---|---|---|---|---|
| | 2 hr | 4 hr | 8 hr | 12 hr | 24 hr |
| 29$^1$ | 133 | 278 | 532 | 720 | 1090 |
| 30$^2$ | 40 | 130 | 336 | 516 | 904 |
| 31 | 419 | 801 | 1316 | 1664 | 2281 |
| 32 | 202 | 425 | 743 | 953 | 1325 |
| 33 | 374 | 829 | 1455 | 1843 | 2432 |
| 34 | 400 | 812 | 1332 | 1647 | 2269 |
| 35 | 591 | 1191 | 1970 | 2480 | 3314 |
| 36 | 137 | 270 | 495 | 682 | 1133 |
| 37 | 328 | 649 | 1099 | 1409 | 1944 |

$^1$These patches were allowed to equilibrate for 4 hours prior to the commencement of the skin penetration test
$^2$These patches were tested immediately after the final lamination and die cutting.

EXAMPLE 28

The upper (skin distal) portion of the transdermal delivery device was prepared as follows. Dry adhesive (332.05 g of isooctyl acrylate:acrylamide:vinyl acetate 75:5:20), (S)-3-methyl-5-(1-methyl-2-pyrrolidinyl)isoxazole (115.46 g) and solvent (831.07 g of ethyl acetate:methanol 90:10) were placed in order in a glass jar. The jar was agitated on a platform shaker for about 24 hours. The formulation was allowed to stand until all air bubbles had dissipated. The formulation was knife coated at a thickness of 32 mils (813 μm) onto a SCOTCHPAK™ 1022 fluoropolymer coated release liner. The coated release liner was allowed to air dry at ambient temperature for 20 minutes then it was immediately laminated to the polyester side of SCOTCHPAK™ 1109 polyester film laminate (available from 3M).

The lower portion of the transdermal delivery device was prepared as follows. A coating formulation containing isooctyl acrylate:acrylamide:vinyl acetate 75:5:20 copolymer in ethyl acetate:methanol 90:10 (35 percent solids) was knife coated at a thickness of 7 mils (178 μm) onto a SCOTCHPAK™ 1022 fluoropolymer coated release liner. The coated release liner was dried at 110° F. (43° C.) for 4 minutes, at 185° F. (85° C.) for 2 minutes and then at 225° F. (107° C.) for 2 minutes. The dried material was allowed to cool to ambient temperature, then it was laminated to the corona treated surface of a 3 mil (76 μm) low density polyethylene film (COTRAN™ 9720).

The release liner was removed from the upper portion then it was laminated onto the low density polyethylene film surface of the lower portion. As initially prepared, the resulting composite consisted of five layers: a backing, a first adhesive layer containing 25.8 percent by weight of (S)-3-methyl-5-(1-methyl- 2-pyrrolidinyl)isoxazole, a low density polyethylene membrane, a second adhesive layer that did not contain drug, and a release liner. Patches were die cut from the composite. The patches were allowed to equilibrate for 48 hours prior to the commencement of skin penetration testing. Skin penetration (human cadaver skin) data is shown in Table 16 below. Each value is the average of three independent determinations.

TABLE 16

| Cumulative Amount Penetrating (μm/cm²) | | | | |
| --- | --- | --- | --- | --- |
| 2 hr | 4 hr | 8 hr | 12 hr | 24 hr |
| 613 | 897 | 1269 | 1549 | 2260 |

EXAMPLE 39

An upper portion of a transdermal delivery device identical with that of Example 38 was prepared.

The lower portion was prepared by knife coating the formulation prepared in Example 38 for the upper portion at a thickness of 17 mils (432 μm) onto a SCOTCHPAK™ 1022 fluoropolymer coated release liner. The coated release liner was allowed to dry at ambient temperature for 20 minutes before being laminated to the matte side of a 9% EVA membrane (COTRAN™ 9702 membrane).

The release liner was removed from the upper portion and it was laminated to the membrane side of the lower portion. The resulting composite consisted of five layers: a backing; a first adhesive layer containing 25.8 percent by weight of (S)-3-methyl-5-(1-methyl- 2-pyrrolidinyl)isoxazole; a 9% EVA membrane; a second adhesive layer containing 25.8 percent by weight of (S)-3-methyl-5-(1-methyl-2-pyrrolidinyl)isoxazole; and a release liner. The composite was die cut into patches. The patches were allowed to equilibrate for 48 hours prior to the commencement of skin penetration testing. Skin penetration (human cadaver skin) data is shown in Table 17 below. Each value is the average of three separate determinations.

TABLE 17

| Cumulative Amount Penetrating (μm/cm²) | | | | |
| --- | --- | --- | --- | --- |
| 2 hr | 4 hr | 8 hr | 12 hr | 24 hr |
| 1420 | 2330 | 3431 | 4185 | 5571 |

EXAMPLES 40–45

Dry adhesive (28.6274 g of isooctyl acrylate:acrylamide:vinyl acetate 75:5:20 copolymer), (S)-3-methyl-5-(1-methyl-2-pyrrolidinyl)isoxazole (9.9572 g), ethyl acetate (64.78 g) and methanol (7.20 g) were placed in a glass jar. The jar was capped then agitated on a platform shaker until a uniform formulation was obtained.

The upper portion of the transdermal delivery device was prepared by knife coating the formulation at a thickness of 30 mils (762 μm) on a SCOTCHPAK™ 1022 fluoropolymer coated release liner. The coated release liner was allowed to dry for 60 minutes at ambient temperature then it was laminated to the polyester side of SCOTCHPAK™ 1109 polyester film laminate.

The lower portion was prepared by knife coating the formulation at a thickness of 17 mil (432 μm) onto a SCOTCHPAK™ 1022 fluoropolymer coated release liner. The coated release liner was allowed to dry at ambient temperature for 20 minutes then it was laminated to one of the membranes shown in Table 18 below.

The release liner was removed from the upper portion and then it was laminated to the membrane surface of the lower portion. The resulting composite contained a backing, a first adhesive layer, a membrane, a second adhesive layer and a release liner. Both adhesive layers contained 25.8 percent by weight of (S)-3-methyl-5-(1-methyl-2-pyrrolidinyl)isoxazole based on the total weight of drug and adhesive copolymer. The composite was die cut into patches. Skin penetration (human cadaver skin) data is shown in Table 19 below. Each value is the average of three separate determinations.

TABLE 18

| Example Number | Membrane |
| --- | --- |
| 40 | Nylon scrim[1] |
| 41 | Polyurethane film[2] (2 mil/51 μm) |
| 42 | Macroporous polyethylene[3] |
| 43 | Microporous polyethylene[4] (2 mil/51 μm) |
| 44 | 19% EVA[5] (2 mil/51 μm) |
| 45 | 19% EVA[5] (4 mil/102 μm) |

[1]CEREX ™ HC1616012 (Fiber Web North America, Inc., Simpsonville, SC)
[2]Prepared from Dow Medical Grade 2363-80AE Resin
[3]DELNET ™ CSD0707-25 high density polyethylene thermal formed netting (Applied Extrusion Technologies Inc., Middletown, DE)
[4]COTRAN ™ 9710
[5]Prepared from ULTRATHENE ™ UE631-000 from Quantum Chemical

TABLE 19

| Example Number | Cumulative Amount Penetrating (μm/cm²) | | | | |
| --- | --- | --- | --- | --- | --- |
| | 2 hr | 4 hr | 8 hr | 12 hr | 24 hr |
| 40 | 897 | 1705 | 2916 | 3640 | 4776 |
| 41 | 1022 | 2219 | 3710 | 4680 | 6140 |
| 42 | 1114 | 2246 | 3738 | 4649 | 5981 |
| 43 | 1197 | 2619 | 4372 | 5274 | 6485 |

TABLE 19-continued

| Example Number | Cumulative Amount Penetrating (μm/cm²) | | | | |
|---|---|---|---|---|---|
| | 2 hr | 4 hr | 8 hr | 12 hr | 24 hr |
| 44 | 919 | 1918 | 3239 | 4092 | 5525 |
| 45 | 1315 | 2383 | 3578 | 4417 | 5897 |

EXAMPLES 46–51

Dry adhesive (25.6671 g of isooctyl acrylate:acrylamide:vinyl acetate 75:5:20 copolymer), (S)-3-methyl-5-(1-methyl-2-pyrrolidinyl)isoxazole (6.9005 g), ethyl acetate (54.79 g) and methanol (6.09 g) were placed in a glass jar. The jar was capped then agitated on a platform shaker until a uniform formulation was obtained.

The upper portion of a transdermal delivery device was prepared by knife coating the formulation at a thickness of 28 mils (711 μm) on a SCOTCHPAK™ 1022 fluoropolymer coated release liner. The coated release liner was allowed to dry for 60 minutes at ambient temperature then it was laminated to the polyester side of SCOTCHPAK™ 1109 polyester film laminate.

The lower portion was prepared by knife coating the formulation at a thickness of 8 mil (203 μm) onto a SCOTCHPAK™ 1022 fluoropolymer coated release liner. The coated release liner was allowed to dry at ambient temperature for 20 minutes then it was laminated to one of the membranes shown in Table 20 below.

The release liner was removed from the upper portion and it was laminated to the membrane surface of the lower portion. The resulting composite contained a backing, a first adhesive layer, a membrane, a second adhesive layer and a release liner. Both adhesive layers contained 21.1 percent by weight of (S)-3-methyl-5-(1-methyl-2-pyrrolidinyl)isoxazole based on the total weight of drug and adhesive copolymer. The composite was die cut into patches. Skin penetration (human cadaver skin) data is shown in Table 21 below. Each value is the average of three independent determinations.

TABLE 20

| Example Number | Membrane |
|---|---|
| 46 | Polyurethane film[1] (2 mil/51 μm) |
| 47 | 4.5% EVA film[2] (3 mil/76 μm) |
| 48 | 4.5% EVA film[2] (2 mil/51 μm) |
| 49 | Linear low density polyethylene film[3] (3 mil/76 μm) |
| 50 | High density polyethylene film[4] (3 mil/76 μm) |
| 51 | Low density polyethylene film[5] (3 mil/76 μm) |

[1]Prepared from Dow Medical Grade 2363-80AE Resin
[2]Prepared from NATR 198 Resin, Quantum Chemical
[3]Prepared from DOWLEX ™ 2035, Dow Chemical Company
[4]Prepared from 9720 resin, Dow Chemical Company
[5]COTRAN ™ 9720, 3M Company

TABLE 21

| Example Number | Cumulative Amount Penetrating (μm/cm²) | | | | |
|---|---|---|---|---|---|
| | 2 hr | 4 hr | 8 hr | 12 hr | 24 hr |
| 46 | 537 | 1151 | 2108 | 2734 | 3539 |

TABLE 21-continued

| Example Number | Cumulative Amount Penetrating (μm/cm²) | | | | |
|---|---|---|---|---|---|
| | 2 hr | 4 hr | 8 hr | 12 hr | 24 hr |
| 47 | 668 | 1087 | 1472 | 1749 | 2404 |
| 48 | 616 | 1037 | 1475 | 1802 | 2502 |
| 49 | 580 | 976 | 1322 | 1544 | 2028 |
| 50 | 623 | 915 | 1068 | 1117 | 1210 |
| 51 | 623 | 992 | 1244 | 1568 | 2093 |

EXAMPLE 53

Dry adhesive (11.9008 g of isooctyl acrylate:acrylamide:vinyl acetate 75:5:20 copolymer), (S)-3-methyl-5-(1-methyl-2-pyrrolidinyl)isoxazole (3.0672 g), ethyl acetate (25.04 g) and methanol (2.87 g) were combined and agitated to provide a uniform formulation. The formulation was knife coated at a thickness of 21 mil (533 μm) onto a release liner. The coated release liner was allowed to dry at ambient temperature for 1 hour.

The upper (skin distal) portion of a transdermal delivery device was prepared by laminating a portion of the dried coated release liner to the polyester side of SCOTCHPAK™ 1109 polyester film laminate. The release liner was removed and the backing/adhesive laminate was laminated to another portion of the dried coated release liner.

The lower portion of a transdermal delivery device was prepared by laminating a portion of the dried coated release liner to a 2 mil (51 μm) 9% EVA membrane (COTRAN™ 9703).

The release liner was removed from the upper portion and it was laminated to the membrane surface of the lower portion. In the resulting composite, the first adhesive layer was twice as thick as the second adhesive layer and both contained 20.5 percent by weight of (S)-3-methyl-5-(1-methyl-2-pyrrolidinyl)isoxazole. The composite was die cut into patches. The skin penetration (human cadaver skin) data is shown in Table 22 below. Each value is the average of two independent determinations.

TABLE 22

| Cumulative Amount Penetrating (μm/cm²) | | | | |
|---|---|---|---|---|
| 2 hr | 4 hr | 8 hr | 12 hr | 24 hr |
| 440 | 945 | 1722 | 2312 | 3628 |

EXAMPLE 53

Transdermal delivery devices were prepared according to the method of Example 52 except that a 3 mil (76 μm) 19% EVA membrane (prepared from ULTRATHENE™ UE631-000, Quantum Chemical) was used. Skin penetration (human cadaver skin) data is shown in Table 23 below. Each value is the average of three independent determinations.

TABLE 23

| Cumulative Amount Penetrating (μm/cm²) | | | | |
|---|---|---|---|---|
| 2 hr | 4 hr | 8 hr | 12 hr | 24 hr |
| 548 | 1160 | 2117 | 2920 | 4463 |

EXAMPLES 54–76

A set of transdermal delivery devices was prepared in which the weight percent of (S)-3-methyl-5-(1-methyl-2-pyrrolidinyl)isoxazole in the adhesive layer, the thickness of the first and second adhesive layers and the membrane composition were varied.

A coating formulation (Formulation A) was prepared by placing dry adhesive (2.7446 g of isooctyl acrylate:acrylamide:vinyl acetate 75:5:20 copolymer), drug (0.2548 g of (S)-3-methyl-5-(1-methyl-2-pyrrolidinyl)isoxazole), ethyl acetate (5.017 g) and methanol (0.557 g) in order into a glass jar. The jar was capped, wrapped in aluminum foil and then agitated on a platform shaker to obtain a uniform formulation. When this formulation was coated onto a release liner and dried, the resulting adhesive layer contained 8.5 percent by weight of drug based on the total weight of drug and adhesive.

Using the same method, four additional coating formulations were prepared. In each formulation the drug was (S)-3-methyl-5-(1-methyl-2-pyrrolidinyl)isoxazole, the adhesive was isooctyl acrylate:acrylamide:vinyl acetate 75:5:20 copolymer, the solvent was 90:10 ethyl acetate:methanol and the percent solids in the formulation was 35 percent. The formulation designation and the weight percent of drug in the adhesive layer after coating and drying the formulation are as follows: Formulation B—13.0 percent; Formulation C—17.5 percent; Formulation D—22.0 percent; and Formulation E—26.5 percent.

The upper portion of the transdermal delivery device was prepared by knife coating the formulation at the designated thickness onto a SCOTCHPAK™ 1022 fluoropolymer coated release liner. The coated release liner was allowed to dry at ambient temperature for 20 [4 mil (102 μm) and 8 mil (203 μm) coatings] or 30 minutes [12–20 mil (305–508 μm) coatings] then it was laminated to the polyester side of SCOTCHPAK™ 1109 polyester film laminate.

The lower portion of the transdermal delivery device was prepared by knife coating the formulation at the designated thickness onto a SCOTCHPAK™ 1022 fluoropolymer coated release liner. The coated release liner was allowed to dry at ambient temperature for 60 minutes then it was laminated to the designated membrane.

Composites were assembled by removing the release liner from the appropriate upper portion and laminating it to the membrane surface of the appropriate lower portion. The resulting composites contained a backing, a first adhesive layer, a membrane, a second adhesive layer and a release liner. The weight percent of drug was the same in both layers of adhesive. The coating formulation used, the coating thickness for the upper and lower portions, and the membrane used to prepare each composite are shown in Table 24 below. Skin penetration (human cadaver skin) data is shown in Table 25 below. Unless otherwise indicated, each value is the average of three independent determinations.

TABLE 24

| Example Number | Formulation | Coating Thickness (μm) Lower | Coating Thickness (μm) Upper | Membrane |
|---|---|---|---|---|
| 54 | A | 305 | 737 | 9% EVA[1] |
| 55 | B | 203 | 660 | LDPE[2] |
| 56 | B | 203 | 660 | 19% EVA[3] |
| 57 | B | 203 | 813 | LDPE |
| 58 | B | 203 | 813 | 19% EVA |
| 59 | B | 406 | 660 | LDPE |
| 60 | B | 406 | 660 | 19% EVA |
| 61 | B | 406 | 813 | LDPE |
| 62 | B | 406 | 813 | 19% EVA |
| 63 | C | 102 | 737 | 9% EVA |
| 64 | C | 305 | 584 | 9% EVA |
| 65 | C | 305 | 737 | 9% EVA |
| 66 | C | 305 | 889 | 9% EVA |
| 67 | C | 508 | 737 | 9% EVA |
| 68 | D | 203 | 660 | LDPE |
| 69 | D | 203 | 660 | 19% EVA |
| 70 | D | 203 | 813 | LDPE |
| 71 | D | 203 | 813 | 19% EVA |
| 72 | D | 406 | 660 | LDPE |
| 73 | D | 406 | 660 | 19% EVA |
| 74 | D | 406 | 813 | LDPE |
| 75 | D | 406 | 813 | 19% EVA |
| 76 | E | 305 | 737 | 9% EVA |

[1]COTRAN™ 9702
[2]Liner low density polyethylene film COTRAN™ 9720
[3]Prepared from ULTRATHENE™ UE631-000, Quantum Chemical

TABLE 25

| Example Number | Cumulative Amount Penetrating (μm/cm$^2$) 2 hr | 4 hr | 8 hr | 12 hr | 24 hr |
|---|---|---|---|---|---|
| 54 | 266[1] | 474[1] | 661[1] | 777[1] | 980[1] |
| 55 | 336 | 524 | 705 | 836 | 1138 |
| 56 | 241 | 479 | 829 | 1085 | 1553 |
| 57 | 340 | 534 | 718 | 838 | 1178 |
| 58 | 422 | 757 | 1219 | 1575 | 2281 |
| 59 | 408 | 792 | 1156 | 1354 | 1736 |
| 60 | 520 | 924 | 1437 | 1818 | 2455 |
| 61 | 406 | 792 | 1171 | 1369 | 1739 |
| 62 | 460 | 892 | 1451 | 1836 | 2623 |
| 63 | 391[1] | 559[1] | 763[1] | 992[1] | 1421[1] |
| 64 | 609[1] | 1056[1] | 1415[1] | 1648[1] | 2064[1] |
| 65 | 731[3] | 1244[3] | 1708[3] | 1981[3] | 2377[3] |
| 66 | 698[1] | 1200[1] | 1589[1] | 1817[1] | 2326[1] |
| 67 | 792[1] | 1495[1] | 2098[1] | 2423[1] | 2936[1] |
| 68 | 658 | 1014 | 1340 | 1566 | 2161 |
| 69 | 969 | 1549 | 2314 | 2776 | 3402 |
| 70 | 794 | 1169 | 1504 | 1768 | 2399 |
| 71 | 715 | 1289 | 2095 | 2758 | 3834 |
| 72 | 989 | 1697 | 2326 | 2681 | 3318 |
| 73 | 938 | 1704 | 2625 | 3218 | 4284 |
| 74 | 824 | 1547 | 2231 | 2569 | 3238 |
| 75 | 959 | 1749 | 2755 | 3509 | 4604 |
| 76 | 1256[2] | 1943[2] | 2533[2] | 2854[2] | 3641[2] |

[1]Average of 6 independent determinations
[2]Average of 5 independent determinations
[3]Average of 18 independent determinations

EXAMPLE 77

Dry adhesive (818.1 g of isooctyl acrylate:acrylamide:vinyl acetate 74:6:20 copolymer), (S)-3-methyl-5-(1-methyl-2-pyrrolidinyl)isoxazole (284.4 g), ethyl acetate (1842.8 g) and methanol (204.7 g) were placed in a glass jar. The jar was capped then agitated on a platform shaker until a uniform formulation was obtained.

The upper portion of the transdermal delivery device was prepared by knife coating the formulation at a thickness of 32 mils (813 μm) onto a SCOTCHPAK™ 1022 fluoropolymer coated release liner. The coated release liner was allowed to dry for 60 minutes at ambient temperature then it was laminated to the polyester side of SCOTCHPAK™ 1109 polyester film laminate.

The lower portion was prepared by knife coating the formulation at a thickness of 16 mil (406 μm) onto a SCOTCHPAK™ 1022 fluoropolymer coated release liner. The coated release liner was allowed to dry at ambient temperature for 60 minutes then it was laminated to the matte side of a COTRAN™ 9702 membrane.

The release liner was removed from the upper portion and then it was laminated to the membrane surface of the lower portion. The resulting composite contained a backing, a first adhesive layer, a membrane, a second adhesive layer and a release liner. Both adhesive layers contained 25.8 percent by weight of (S)-3-methyl-5-(1-methyl-2-pyrrolidinyl)isoxazole based on the total weight of drug and adhesive copolymer. The composite was die cut into patches. Skin penetration (human cadaver skin)data is shown in Table 26 below. Each value is the average of three independent determinations.

TABLE 26

| Cumulative Amount Penetrating (μm/cm$^2$) | | | | |
| --- | --- | --- | --- | --- |
| 2 hr | 4 hr | 8 hr | 12 hr | 24 hr |
| 551 | 1110 | 1912 | 2548 | 3833 |

EXAMPLES 78–82

The penetration of (S)-3-methyl-5-(1-methyl-2-pyrrolidinyl)isoxazole from excipient solutions through human cadaver skin was assessed as follows. Solutions containing 30 mg of (S)-3-methyl-5-(1-methyl-2-pyrrolidinyl) isoxazole per mL of excipient were prepared by combining 240 mg of (S)-3-methyl-5-(1-methyl- 2-pyrrolidinyl) isoxazole with 8 mL of one of the excipients listed in Table 27 below and agitating the mixture on a platform shaker until a solution was obtained. Skin penetration was measured using the test method described above with the following changes: a patch was not placed on the skin prior to cell assembly and after the cell was assembled a 2 mL portion of the solution containing drug in excipient was added to the upper portion of the cell. The skin penetration (human cadaver skin) data is shown in Table 28 below. Each value is the average of two independent determinations.

TABLE 27

| Example Number | Excipient |
| --- | --- |
| 78 | Lauryl alcohol |
| 79 | Ethyl oleate |
| 80 | Oleic acid |
| 81 | Oleyl alcohol |
| 82 | Poly(ethylene glycol-400) monolaurate |
| Control | 0.1 M Phosphate buffer (pH 6) |

TABLE 28

| Example Number | Cumulative Amount Penetrating (μm/cm$^2$) | | | | | |
| --- | --- | --- | --- | --- | --- | --- |
| | 2 hr | 4 hr | 8 hr | 12 hr | 24 hr | 48 hr |
| 78 | 0 | 23 | 130 | 287 | 1146 | 3342 |
| 79 | 19 | 87 | 286 | 524 | 1371 | 2967 |
| 80 | 0 | 0 | 14 | 32 | 122 | 356 |
| 81 | 0 | 18 | 90 | 191 | 627 | 1613 |
| 82 | 0 | 1 | 17 | 41 | 146 | 409 |
| Control | 2 | 22 | 80 | 164 | 482 | 868 |

What is claimed is:

1. A transdermal delivery device comprising:
   (A) a backing;
   (B) an adhesive layer adhered to one surface of the backing and comprising a homogeneous mixture of
      (1) a copolymer comprising
         (a) about 80 to 98 percent by weight of an alkyl acrylate or methacrylate containing 4 to 10 carbon atoms in the alkyl group, based on the weight of all monomers in the copolymer; and
         (b) about 2 to 20 percent by weight of a monomer selected from the group consisting of acrylic acid, methacrylic acid, an alkyl acrylate or methacrylate containing 1 to 3 carbon atoms in the alkyl group, acrylamide, methacrylamide, a lower alkyl substituted acrylamide, diacetone acrylamide and N-vinyl-2-pyrrolidone, based on the weight of all monomers in the copolymer; and
      (2) about 5 to about 35 percent by weight based on the total weight of the adhesive layer of (S)-3-methyl-5-(1-methyl- 2-pyrrolidinyl)isoxazole.

2. A transdermal delivery device according to claim 1 wherein the (S)-3-methyl-5-(1-methyl-2-pyrrolidinyl)isoxazole is present in an amount of about 10 to about 30 percent by weight based on the total weight of the adhesive layer.

3. A transdermal delivery device according to claim 1, wherein the copolymer comprises isooctyl acrylate.

4. A transdermal delivery device according to claim 1, wherein the copolymer comprises acrylic acid.

5. A transdermal delivery device according to claim 1, wherein the adhesive layer further comprises a skin penetration enhancer.

6. A transdermal delivery device comprising:
   (A) a backing;
   (B) an adhesive layer adhered to one surface of the backing and comprising a homogeneous mixture of
      (1) a copolymer comprising
         (a) about 60 to 80 percent by weight of an alkyl acrylate or methacrylate containing 4 to 10 carbon atoms in the alkyl group, based on the weight of all monomers in the copolymer;
         (b) about 4 to 9 percent by weight of a monomer selected from the group consisting of acrylic acid, methacrylic acid, an alkyl acrylate or methacrylate containing 1 to 3 carbon atoms in the alkyl group, acrylamide, methacrylamide, a lower alkyl substituted acrylamide, diacetone acrylamide and N-vinyl-2-pyrrolidone, based on the weight of all monomers in the copolymer; and
         (c) about 15 to 35 percent by weight of vinyl acetate, based on the weight of all monomers in the copolymer; and
      (2) about 5 to about 35 percent by weight based on the total weight of the adhesive layer of (S)-3-methyl-5-(1-methyl- 2pyrrolidinyl)isoxazole.

7. A transdermal delivery device according to claim 6, wherein the (S)-3-methyl-5-(1-methyl-2-pyrrolidinyl)isoxazole is present in an amount of about 10 to about 30 percent by weight based on the total weight of the adhesive layer.

8. A transdermal delivery device according to claim 6, wherein the copolymer comprises the acrylate or methacrylate in an amount of about 70 to 80 percent by weight based on the total weight of all monomers in the copolymer.

9. A transdermal delivery device according to claim 6, wherein the copolymer comprises isooctyl acrylate.

10. A transdermal delivery device according to claim 6, wherein the copolymer comprises acrylamide.

11. A transdermal delivery device according to claim 6, wherein the adhesive layer further comprises a skin penetration enhancer.

12. A transdermal delivery device comprising:
(A) a backing;
(B) a first adhesive layer adhered to one surface of the backing and comprising an adhesive selected from the group consisting of:
  (1) a copolymer comprising
    (a) about 80 to 98 percent by weight of an alkyl acrylate or methacrylate containing 4 to 10 carbon atoms in the alkyl group, based on the weight of all monomers in the copolymer; and
    (b) about 2 to 20 percent by weight of a monomer selected from the group consisting of acrylic acid, methacrylic acid, an alkyl acrylate or methacrylate containing 1 to carbon atoms in the alkyl group, acrylamide, methacrylamide, a lower alkyl substituted acrylamide, diacetone acrylamide and N-vinyl-2-pyrrolidone, based on the weight of all monomers in the copolymer; and
  (2) a copolymer comprising
    (a) about 60 to 80 percent by weight of an alkyl acrylate or methacrylate containing 4 to 10 carbon atoms in the alkyl group, based on the weight of all monomers in the copolymer;
    (b) about 4 to 9 percent by weight of a monomer selected from the group consisting of acrylic acid, methacrylic acid, an alkyl acrylate or methacrylate containing 1 to carbon atoms in the alkyl group, acrylamide, methacrylamide, a lower alkyl substituted acrylamide, diacetone acrylamide and N-vinyl-2-pyrrolidone, based on the weight of all monomers in the copolymer; and
    (c) about 15 to 35 percent by weight of vinyl acetate, based on the weight of all monomers in the copolymer;
(C) a second adhesive layer comprising an adhesive selected from the group consisting of:
  (1) a copolymer comprising
    (a) about 80 to 98 percent by weight of an alkyl acrylate or methacrylate containing 4 to 10 carbon atoms in the alkyl group, based on the weight of all monomers in the copolymer; and
    (b) about 2 to 20 percent by weight of a monomer selected from the group consisting of acrylic acid, methacrylic acid, an alkyl acrylate or methacrylate containing 1 to 3 carbon atoms in the alkyl group, acrylamide, methacrylamide, a lower alkyl substituted acrylamide, diacetone acrylamide and N-vinyl-2-pyrrolidone, based on the weight of all monomers in the copolymer; and
  (2) a copolymer comprising
    (a) about 60 to 80 percent by weight of an alkyl acrylate or methacrylate containing 4 to 10 carbon atoms in the alkyl group, based on the weight of all monomers in the copolymer;
    (b) about 4 to 9 percent by weight of a monomer selected from the group consisting of acrylic acid, methacrylic acid, an alkyl acrylate or methacrylate containing 1 to 3 carbon atoms in the alkyl group, acrylamide, methacrylamide, a lower alkyl substituted acrylamide, diacetone acrylamide and N-vinyl-2-pyrrolidone, based on the weight of all monomers in the copolymer; and
    (c) about 15 to 35 percent by weight of vinyl acetate, based on the weight of all monomers in the copolymer; and
(D) a membrane between the first and second adhesive layers, the membrane being permeable to (S)-3-methyl-5-(1-methyl-2-pyrrolidinyl)isoxazole, wherein at least one of said first and second adhesive layers further comprises about 5 to about 35 percent by weight based on the total weight of the adhesive layer of (S)-3-methyl-5-(1-methyl-2-pyrrolidinyl)isoxazole in admixture therewith.

13. A transdermal delivery device according to claim 12, wherein the (S)-3-methyl-5-(1-methyl-2-pyrrolidinyl)isoxazole is present in both the first and second adhesive layers in an amount of about 10 to 30 percent by weight based on the total weight of each such first and second adhesive layer.

14. A transdermal delivery device according to claim 12, wherein the both the first and second adhesive layer comprise a copolymer comprising:
(a) about 80 to 98 percent by weight of an alkyl acrylate or methacrylate containing 4 to 10 carbon atoms in the alkyl group, based on the weight of all monomers in the copolymer; and
(b) about 2 to 20 percent by weight of a monomer selected from the group consisting of acrylic acid, methacrylic acid, an alkyl acrylate or methacrylate containing 1 to 3 carbon atoms in the alkyl group, acrylamide, methacrylamide, a lower alkyl substituted acrylamide, diacetone acrylamide and N-vinyl-2-pyrrolidone, based on the weight of all monomers in the copolymer.

15. A transdermal delivery device according to claim 14, wherein the copolymer in the first and second adhesive layers comprises isooctyl acrylate.

16. A transdermal delivery device according to claim 14, wherein the copolymer in the first and second adhesive layers comprises acrylic acid.

17. A transdermal delivery device according to claim 12, wherein both the first and second adhesive layers further comprise a skin penetration enhancer.

18. A transdermal delivery device according to claim 12, wherein the membrane comprises a material selected from the group consisting of low density polyethylene, linear low density polyethylene, high density polyethylene, polyurethane, nylon and ethylene/vinyl acetate copolymers.

19. A transdermal delivery device according to claim 12, wherein the membrane is a continuous film.

20. A transdermal delivery device according to claim 12, wherein the membrane is a microporous membrane.

21. A transdermal delivery device according to claim 12, wherein the membrane is a rate controlling membrane.

22. A transdermal delivery device according to claim 12, wherein the both the first and second adhesive layer comprise a copolymer comprising:
(a) about 60 to 80 percent by weight of an alkyl acrylate or methacrylate containing 4 to 10 carbon atoms in the alkyl group, based on the weight of all monomers in the copolymer;
(b) about 4 to 9 percent by weight of a monomer selected from the group consisting of acrylic acid, methacrylic acid, an alkyl acrylate or methacrylate containing 1 to 3 carbon atoms in the alkyl group, acrylamide, methacrylamide, a lower alkyl substituted acrylamide, diacetone acrylamide and N-vinyl-2pyrrolidone, based on the weight of all monomers in the copolymer; and (c) about 15 to 35 percent by weight of vinyl acetate, based on the weight of all monomers in the copolymer.

23. A transdermal delivery device according to claim 21, wherein the copolymer in the first and second adhesive layers comprises isooctyl acrylate.

24. A transdermal delivery device according to claim 22, wherein the copolymer in the first and second adhesive layers comprises acrylamide.

25. A transdermal delivery device according to claim 23, wherein both the copolymer in the first and second adhesive layers comprises about 75% by weight isooctyl acrylate, about 5% by weight acrylamide, and about 20% by weight vinyl acetate.

26. A transdermal delivery device according to claim 24, wherein both the first and second adhesive layer comprise (S)-3-methyl-5-(1-methyl-2-pyrrolidinyl)isoxazole in an amount of about 25% by weight based on the total weight of the respective adhesive layer.

27. A method of transdermal delivery of the compound (S)-3-methyl-5-(1-methyl-2-pyrrolidinyl)isoxazole, comprising the steps of:

(i) placing a transdermal delivery device according to claim 1 on the skin of a patient; and (ii) allowing said device to remain in place for a time sufficient to allow (S)-3-methyl-5-(1-methyl- 2-pyrrolidinyl)isoxazole to penetrate the skin of the patient.

* * * * *

UNITED STATES PATENT AND TRADEMARK OFFICE
CERTIFICATE OF CORRECTION

PATENT NO.: 5,494,680

DATED: Feb. 27, 1996

INVENTOR(S): Timothy A. Peterson

It is certified that error appears in the above-identified patent and that said Letters Patent is hereby corrected as shown below:

Column 22, line 63, "5-(1-methyl-2pyrrolidinyl)isoxazole" should be --5-(1-methyl-2-pyrrolidinyl)isoxazole--;

Column 23, line 25, "1 to carbon" should be --1 to 3 carbon--;

Column 23, line 38, "1 to carbon" should be --1 to 3 carbon--;

Column 24, line 12, "5-( 1-methyl" should be --5-(1-methyl--;

Column 24, line 16, "methyl- 2-pyrrolidinyl" should be --methyl-2-pyrrolidinyl--; and Column 25, line 3, "N-vinyl-2pyrrolidone," should be --N-vinyl-2-pyrrolidone--.

Signed and Sealed this

Twenty-seventh Day of October, 1998

*Attest:*

BRUCE LEHMAN

*Attesting Officer*      *Commissioner of Patents and Trademarks*